United States Patent [19]
Politi et al.

[11] Patent Number: 5,846,755
[45] Date of Patent: Dec. 8, 1998

[54] METHOD FOR DETERMINING THE THERAPEUTIC ACTIVITY OF METALLOPROTEINASE INHIBITOR COMPOUNDS

[75] Inventors: Vencenzo Politi; Silvana D'Alessio; Giovanni Di Stazio; Giovanna De Luca; Mario Materazzi, all of Rome, Italy

[73] Assignee: Polifarma S.p.A., Rome, Italy

[21] Appl. No.: 693,021

[22] Filed: Aug. 6, 1996

[30] Foreign Application Priority Data

Aug. 7, 1995 [IT] Italy ................................. RM95A0557

[51] Int. Cl.[6] ...................................................... C12Q 1/37
[52] U.S. Cl. .................................................. 435/23; 435/24
[58] Field of Search .................................. 514/18; 435/23, 435/24

[56] References Cited

U.S. PATENT DOCUMENTS 5,472,851  12/1995  Pussard née Contant et al. ....... 435/13
5,504,071  4/1996  Politi et al. ................................. 514/18

FOREIGN PATENT DOCUMENTS 758021  2/1996  European Pat. Off. .
92 06198  4/1992  WIPO .

OTHER PUBLICATIONS

Robeva et al. (1991) Biomed. Biochim. Acta, 50(4–5), "Synthetic and Endogenous Inhibitors of Snake Venom Metalloproteinases", pp. 769–773.

Giroux et al. (1981) Toxicon, 19(4), "In Vivo diminution by Chelators of Snake Venom–Provoked Hemorrage and In Vitro Inhibition of Proteolytic Acitivity", pp. 481–492.

Ondetti et al. (1979) The Design of Active–Site Directed Reversible Inhibitors of Exopeptidases in Drug Action and Design: Mechanism–Based Enzyme Inhibitors, Kalman, Ed., published by Elsevier North Holland, Inc., pp. 271–287.

Cushman et al. (1980) Inhibitors of Angiotensin–converting Enzyme in The Renin–Angiotensin System, Johnson and Anderson, Ed., published by Plenum Publishing Corp. New York, pp. 199–225.

Calcagni et al. (1993) Farmaco, 48(9), "Inhibitors of Zn–Dependent Metalloproteases: Synthesis and Activity of N–(2–Furoyl)–Z–$\alpha$, $\beta$–Didehydroeleucyl–L–Tryptophan", pp. 1271–1277.

Bjarnason, Jon. B. et al, Hemmorrhagic Metalloproteinases From Snake Venoms, Pharmac. Ther., vol. 62, pp. 325–372, 1994.

Meier, Juerg et al, Effects of Snake Venoms on Hemostasis, Crictical Reviews in Toxicology, vol. 21, Issue 3, pp. 171–182, 1991.

Jiang, Weiping et al, Families of Metalloendopeptidases and Their Relationships, Febs, vol. 312, No. 2.3, pp. 110–114, 1992.

A. Robeva et al, Synthetic and Endogenous Inhibitors of Snake Venom Metalloproteinases, Biomed. Biochim, Acta 50 (1991) 4–6, pp. 769–773.

Lawrence A. Hite[a] et al, A New Family of Proteinases is Defined By Several Snake Venom Metalloproteinases, Biol. Chem. Hoppe–Seyler, vol. 373, pp. 381–385, Jul. 1992.

*Primary Examiner*—Jon P. Weber
*Attorney, Agent, or Firm*—Browdy and Neimark

[57] ABSTRACT

A method for determining the therapeutic potential of peptidomimetic compounds as inhibitors of zinc-dependent metalloproteinase activity associated with pathological conditions of humans and animals.

4 Claims, No Drawings

METHOD FOR DETERMINING THE THERAPEUTIC ACTIVITY OF METALLOPROTEINASE INHIBITOR COMPOUNDS

BACKGROUND OF THE INVENTION

1. Field Of The Invention

The present invention relates to a method for determining with a high level of accuracy the therapeutic activity in mammals, including man, of a class of peptidomimetic compounds that are inhibitors of metalloproteinase enzymes present in snake venom.

The invention further relates to new compounds of the class indicated above, as well as their therapeutic use in a large number of important human diseases, including tumoral invasion, rheumatoid arthritis, periodontitis, corneal ulcers, multiple sclerosis, aneurism of the aorta, osteoporosis, the cicatrization of wounds, contact dermatitis, arteriosclerosis, septic shock, parasite invasion, hypertension, allergies, defective immune response, Alzheimer's disease, chronic bronco-pulmonitis, pulmonary emphysema, cirrhosis of the liver, dilatational cardiomyopathy and dysfunctions in the reproductive system.

2. Description Of The Related Art

Snake venom may be many types of complex mixtures, containing a wide variety of proteolytic enzymes which digest prey or alter the physiological functions of prey, particularly physiological functions such as the circulatory system. In fact, it is well known that the venom from snakes belonging to the family of the Viperidae have profound effects belonging to the family of the Viperidae have profound effects on the hemostatic and fibrinolytic systems, showing pro-coagulant or, alternatively, anti-coagulant activities (see, for example, *Critical Reviews in Toxicology,* 21:171–182, 1991). In a similar manner, factors that have a powerful inhibiting effect on blood platelet aggregation have been found in snake venom, along with others that interfere with activation of prothrombin or fibrin.

An extremely important class of enzymes found in the venom of snakes belonging to the family Crotalidae are the so-called hemorrhagic factors, or hemorrhaging. These are structurally of use to the snake, as they rapidly induce extensive internal hemorrhages in the victims, causing circulatory collapse and preventing the victim from escaping its fate. The mechanism of the hemorrhagic action is due to the particular ease with which the enzymes are capable of degrading a large number of filiform proteins which bind between them the various vasal endothelial cells, allowing the elements of the blood to escape from the vessels. Recent studies have made it possible to ascertain that the hemorrhagic factors, comprising a large number of enzymes isolated from venom, have an extremely varied molecular weight (usually between 20 and 90 KDa), and often contain a number of functional sub-units delegated for hemorrhagic, blood platelet anti-aggregant and adhesive activities (see, for example, *Pharmacology and Therapeutics,* 62:325–372, 1994). Although their molecular weights differ greatly, the hemorrhagins have several fixed characteristics on the catalytic site, e.g., in the way that zinc bonds to certain amino acids in the protein chain, and the way in which they attack the proteins in the basal membrane of blood vessels.

The presence of zinc in the active site is not exclusive to hemorrhaging, but is characteristic of a wide number of proteolytic enzymes that perform important physiological and pathological functions in animals, from the smallest and most simple to the most highly evolved. Through the study of the sequences in residues from the protein chain and the amino acids involved in zinc bonding it has been possible to obtain a sort of "family tree" for this family of proteases (see, for example, *FEBS Letters,* 312:110–114, 1992). It has, thus, been seen that enzymes belonging to widely differing living beings, such as astatin (extracted from a river crustacean), serratin (obtained from a microorganism), matrixins (present in the organism of mammals, where they have important effects on cell migration and the reconstruction of damaged tissue) and the hemorrhagic factors of snake venom, in reality differ only in one of the four amino acids binding zinc in the active site, and can thus, in a certain sense, be considered as distantly related to each other. However, this does not mean that the functions performed by these enzymes are similar. It has, in fact, been clarified that the proteolytic enzymes of snake venom have no similarity, either structural or functional, with any other protein in the plant or animal world, with the exception of the zinc site. However, they are very similar to each other, and they all appear to derive from a single ancestral gene. This similarity makes it possible to define a new family of proteinases: the snake venom metalloproteinases (see, for example, *Biol. Chem. Hoppe-Seyler,* 373:381–385, 1992).

Citation of any document herein is not intended as an admission that such document is pertinent prior art or is considered material to the patentability of any claim of the present application. Any statement as to content or a date of any document is based on the information available to applicants at the time of filing and does not constitute an admission as to the correctness of such a statement.

SUMMARY OF THE INVENTION

In the program of research that has resulted in the present invention, compounds were initially synthesized that have a powerful inhibitory activity on snake venom metalloproteinases. This was done with the intent of finding substances that are potentially of use to antagonize the toxic and lethal effects in persons suffering from snake bites, but also to evaluate the possible new pharmacological activities deriving from the structural similarities in the active site of venom hemorrhagic factors and other zinc-dependent metalloproteinases (including the matrixins) present in the cells of mammals.

The starting point of the research program was provided by the long-term experience of the applicants in the venom, and by the evidence that (as published in *Biomed. Biochem. Acta,* 50:769–773, 1991) snakes protect themselves from the toxic effects of their own metalloproteinases by the production of two tripeptides, which act as competitive inhibitors of the enzyme. The first step was to carry out the synthesis of a new family of compounds of peptidomimetic nature, wherein the initial tripeptide was replaced by chemical groups capable of improving affinity with the active site of the enzyme. A hemorrhagin was then selected that is particularly sensitive to the proteolytic test used in vitro, purified from the venom of *Crotalus Adamanteus.* In this way a satisfactory model was obtained on which to test the strength of the synthesized compounds. Finally, several of the new peptidomimetic compounds were pharmacologically tested in models which could be used to test for therapeutic uses of the new substances.

The results obtained, which form the basis of the present invention, are totally innovative. The present inventors have found that it is possible to develop a new method for antagonizing the lethal effects of certain classes of snake venom by using the inhibitors of the enzymes produced by snake venom. Moreover, a new system was developed to obtain highly predictive information on important therapeutic activities in humans in a wide range of diseases in which the pathogenic intervention of zinc-dependent metalloproteinases has been demonstrated. These diseases range from tumoral invasion to rheumatoid arthritis, periodontitis, corneal invasion to rheumatoid arthritis, periodontitis, corneal ulcers, multiple sclerosis, aneurism of the aorta, osteoporosis, wound healing, contact dermatitis, arteriosclerosis, septic shock, parasite invasion, hypertension, allergies, defective immune responses, Alzheimer's disease, chronic bronco-pulmonitis, pulmonary emphysema, cirrhosis of the liver, dilatational cardiomyopathy and malfunctions of the reproductive system.

An object of the present invention is, therefore, to provide a method for determining the therapeutic activity in mammals of a peptidomimetic compound to recognize and produce an active drug for human and animal treatment, which comprise the steps of:

(1) conducting a first enzyme inhibition test and determining a first level of inhibitory activity of said compound as an inhibitor of zinc-dependent metalloproteinases extracted from the venom of snakes belonging to the families Crotalidae and Viperidae;

(2) confirming said first level with respect to a threshold level of activity sufficient to define said compound as an inhibitor of said zinc-dependent metalloproteinases from snake venom;

(3) conducting a second enzyme inhibition test and determining a second level of inhibitory activity of said compound as an inhibitor of a zinc-dependent metalloproteinase indigenous in mammals and inducing pathological situations in said mammals;

(4) confirming said second level with respect to a threshold level of activity sufficient to define said compound as an inhibitor of said zinc-dependent metalloproteinase endogenous in mammals; and (5) determining by standard pharmacological tests the activity of said compound with respect to said pathological situation.

The present invention also has the object of providing compounds that can be used for human therapy in a large number of pathological situations, which situations range from snake bite poisoning to the invasion by tumoral cells, rheumatoid arthritis and other forms of inflammation, multiple sclerosis, aneurysms of the aorta, osteoporosis, arteriosclerosis, septic shock, Alzheimer's disease, allergies and so on; that is, any pathological situation in which the predominant pathological agent is a zinc-dependent metalloproteinase, whether produced by snake venom or synthesized within the cells of mammals.

DESCRIPTION OF THE PREFERRED EMBODIMENTS

A characteristic common to the compounds described in the present invention is that they are good inhibitors of the zinc-dependent metalloproteinases which are produced in large numbers by snakes belonging to the species of vipers and rattlesnakes, and which are one of the most important lethal factors resulting from the bites of these snakes.

As is known from a work published by the laboratory of the present inventors (*Biomed. Biochem. Acta*, 50:769–773, 1991), snake venom produce can produce large amounts of small peptides, which probably have the job of inhibiting metalloproteinases so that these do not damage the tissues of the snake itself. However, these inhibitors have an extremely specialized activity, because the enzyme must be freed when it is injected into the victim. Our aim was, therefore, to synthesize compounds which are in some way similar to the peptides found in the venom, but which have a much higher inhibiting activity (approximately 1000 times, in the best cases) and which are capable of being administered orally as a pharmaceutical composition, which includes a pharmaceutically acceptable carrier or excipient, as is the case with normal drugs.

It has now surprisingly been found, and forms the basis of the new method according to the present invention, that there is a close correspondence between inhibition of the enzymes found in snake venom and the pharmacological results obtained in animal models in which the pathological agent was presumed to be a zinc-dependent metalloproteinase produced by the tissues of the mammal, so that it is possible to conclude that snake venom zinc-dependent metalloproteinases form an excellent model for primary screening, and that inhibitors of said enzymes are potentially usable in all pathological situations induced by zinc-dependent metalloproteinases present in the organism of mammals.

As zinc-dependent metalloproteinases suitable for use in the method according to the present invention, the following are particularly indicated: *Crotalus Adamanteus* hemorrhagin, *Crotalus Atrox* hemorrhagin, *Agkistrodon Bilneatus* botropasin and hemorrhagin and a number of Echis Carinatus hemorrhagins extracted from the venom of the respective snakes.

The operation used to determine the level of inhibitory activity of the inhibitor compound on the metalloproteinase enzyme can be a test determining the amount of inhibitor required ($IC_{50}$) to inhibit the enzyme's activity.

A numeric evaluation of the inhibitor activity is thus obtained, allowing selection based on activity level.

As mentioned above, it has been surprisingly found that this high level of inhibitory activity is an extremely reliable indication of the inhibitory activity of the compound in question even in the face of other metalloproteinases of endogenous nature in mammals, the activity of which is responsible for a wide range of disturbances and diseases in man.

The method according to the present invention, therefore, provides an instrument for the production of new drugs with direct and non-casual selection criteria, resulting in a reduction in costs.

On the basis of the method according to the invention, a number of new inhibitor compounds having therapeutic activity against pathological conditions associated with zinc-dependent metalloproteinases have also been discovered.

Additional compounds, which are disclosed in WO 92/00618, are also disclosed here for treatment of pathological conditions associated with zinc-dependent metalloproteinases. These known compounds all belong to the class of metalloproteinase inhibiting peptidomimetic compounds found in snake venom. With regard to these compounds, a further object of the present invention is to provide a pharmaceutical composition that comprises these compounds in combination with pharmaceutically acceptable carriers or excipients and that is effective in the inhibition of metalloproteinases of endogenous origin produced by mammals, including man, and which cause a series of diseases.

The compounds of formulas (1) and (2) can be administered orally in a pharmaceutical composition for the treatment of various pathological conditions associated with zinc-dependent metalloproteinases. The preferred dosage range is between about 10 to 200 mg/day. However, the most preferred dosage will be tailored to the individual subject for the particular condition to be treated as is understood and determinable by one skilled in the relevant arts.

The new compounds according to the invention can be described using the following general formula:

$$X-NH-CH-CO-E \qquad \text{formula (1)}$$
$$\phantom{X-NH-}\vert$$
$$\phantom{X-NH-}CH_2-R_4$$

in which:

E indicates OH, $NH_2$, NHOH, $N(CH_3)OH$, or esters thereof;

$R_4$ is $CH-(CH_3)_2$, indol-2-yl, phenyl, cyclohexyl, $CO-NH_2$, or $(CH_2)_3-NH-Fmoc$;

X is Xa, Xb, Xc, 5-methoxy-1-indanone-3-acetyl, naphthoyl, or homoseryl; and where Xa is $$R_2-Z_1 \overset{X_1}{=\!=\!=} Z_1-R_3$$
$$\phantom{R_2-Z_1}\underset{E_1}{\Vert}\phantom{==}R_1$$

where in $X_1$ is: CH, N, or C—OMe $E_1$ is: CH or N $Z_1$ is: C or N $R_1$ is: CO, $(CH_2)_2-CO$, $SO_2$, $CH_2-CO$, or $S-CH_2-CO$ $R_2$ is: OMe, H, $NO_2$, Cl, OEt, or $CH_3$, with the proviso that when A is N, $R_2$ is not present $R_3$ is: OEt, H, or OMe, with the proviso that when $Z_1$ is N, $R_2$ and $R_3$ are not present Xb is

[structure diagram with $R_7$, $R_8$, $X_2$, $R_5$, $(CH_2)n-R_4$]

wherein $X_2$ is: O, N, or NH n is: 1 or 2

$R_6$ is: H $R_7$ is: H, OH, OMe, or Cl $R_8$ is: H or OMe, $R_9$ is: CO

Xc is

[structure diagram with $E_3$, $X_3$, $R_9$]

where in $X_3$ is: O or $CH_2$ $E_3$ is: O or CH $R_9$ is: CO

Description of the Chemical Synthesis of the Compounds
Abbreviations used for REAGENTS and SOLVENTS

| | |
|---|---|
| HBTU | O-Benzotriazol-1-yl-N,N,N',N'-Tetramethyluronium hexafluorophosphate |
| TEA | Triethylamine |
| SOCl2 | Thionyl chloride |
| DCHA | Dicyclohexylamine |
| DMAP | Dimethylaminopyridine |
| DMF | Dimethylformamide |
| DCC | Dicycloesylcarbodiimide |
| HOBT | 1-Hydroxybenzotriazole |
| TMSCl | Trimethylchloroxylane |
| $CH_2Cl_2$ | Dichloromethane |
| $CH_3CN$ | Acetonitrile |
| (S)—Cyt—OH | (S)-1,2,3,4 tetrahydro-9H-pyrrido[3,4-b]indole-3-carboxylic acid |
| Boc—(L)—Leu—OH | N-(tert-Butoxycarbonyl)-(L)—Leu—OH |
| Boc—(L)—Trp—OH | N-(tert-Butoxycarbonyl)-(L)—Trp—OH |
| Boc—(L)—Phe—OH | N-(tert-Butoxycarbonyl)-(L)—Phe—OH |
| Boc—(L)—Cha—OH | N-(tert-Butoxycarbonyl)-(L)-β-cyclohexyl-Ala—OH |
| Boc—(L)—Asn—OH | N-(tert-Butoxycarbonyl)—(L)—Asn—OH |
| Boc—(L)—Lys(Fmoc)—OH | Na-(tert-Butoxycarbonyl)-Ne-(9-Fluornyl-methoxy-carbonyl)—(L)—Lys—OH |
| PIC | Picolinyl |
| 2-PMTA | (2-Pyrimidylthio)acetyl |
| 4-PTA | (4-Pyridylthio)acetyl |
| 3-APZC | (3-Amino-2-pyrazinyl)carbonyl |
| 7-MBF | 7-Methoxy-2-benzofuroyl |
| 4-MQC | (4-Methoxy-2-quinolyl)carbonyl |
| 5-HIC | (5-hydroxy-indole-2-yl)carbonyl |
| 5-MIC | (5-Methoxy-indole-2-yl)carbonyl |
| 2-FUR | 2-Furoyl |
| 3-FUR | 3-Furoyl |
| 2-BZF | 2-Benzofuroyl |
| 2-QIC | Quinaldyl |
| 2-PZC | Pyrazinoyl |
| 2-MPA | 2-Methoxyphenylacetyl |
| 2-EBZ | 2-Ethoxybenzoyl |
| 5-MPZ | (5-Methyl-Pyrazine-2-yl)carbonyl |
| 6-MNC | 6-Methylnicotinoyl |
| 5-MIA | 5-Methoxy-1-indanone-3-acetyl |
| 2,4-DMB | 2,4-Dimethoxybenzoyl |
| 4-MBZ | 4-Methoxybenzoyl |
| 4-NBZ | 4-Nitrobenzoyl |
| 4-CBZ | 4-Chlorobenzoyl |
| 3-NIC | Nicotinoyl |
| 4-NIC | Isonicotinoyl |
| 3,4-DMB | 3,4-Dimethoxybenzoyl |
| HDC | 3-Phenylpropionyl |
| BZS | Benzenesulphonyl |
| 4-EBZ | 4-Ethoxybenzoyl |
| 1-NAF | 1-Naphtoyl |
| Z | Carbobenzoxy |
| Tiof | 2-thiophenic acid |
| Pirr | pyrrole-2-carboxylic acid |
| MePro | N-methyl-(L)-proline |
| Pip | (L)-pipecolinic-2-carboxylic acid |
| Tfc | (S)-(–)-tetrahydro furane-2-carboxylic acid |

As further inhibitor compounds (disclosed in WO 92/00618) that can be used in the method according to the present invention and in the therapeutic uses that will be described below, the following compounds of formula (2) are presented below.

Compounds of formula (2):

$$Q-B-T \qquad \text{formula (2)}$$

where Q is a monovalent radical of a ring molecule selected from the group comprising

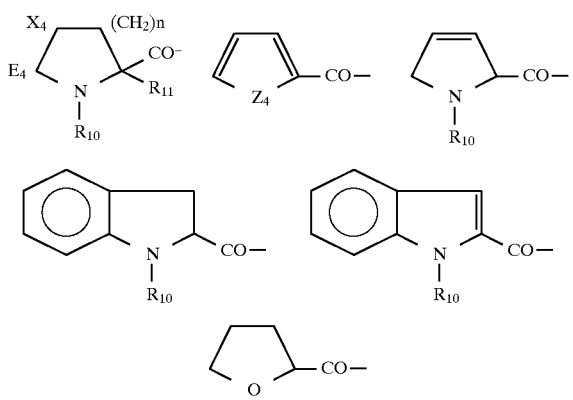

wherein
- $X_4$ is: $CH_2$, S or CHOH;
- n is: 0, 1 or 2;
- $R_{11}$ is: H or $CH_3$;
- $R_{10}$ is: H, $CH_3$ or a generic group that blocks 1' nitrogen atom as used in peptide synthesis and are well known in the art of peptide synthesis, such as CBZ, BOC, Fmoc and acetyl;
- $E_4$ is: $CH_2$ or CO;
- $Z_4$ is: NH, $NCH_3$, O or S;
- B is a bivalent radical of an (L)-alpha-amino acid selected from the group comprising glycine, leucine, alanine or valine; and
- T is a monovalent radical of an aromatic (L)-amino acid selected from the group comprising tryptophan, phenylalanine, phenylglycine, and pharmaceutically acceptable salts, esters and amides thereof;

the compounds

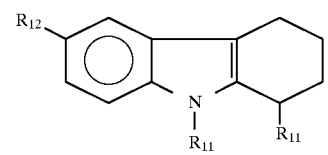 Formula 3

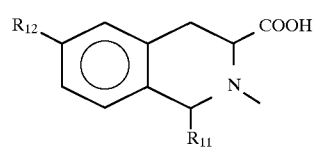 Formula 4

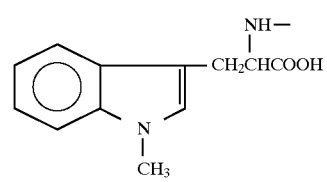 Formula 5

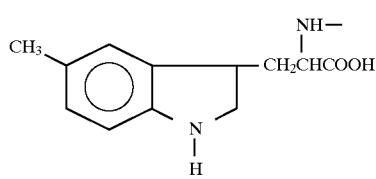 Formula 6 wherein
$R_{11}$ has the meaning indicated above, and
$R_{12}$ can be H, OH, $OCH_3$, or $CH_3$,
and pharmaceutically acceptable salts, esters and amides thereof.

The invention will now be illustrated by the following non-limiting examples.

EXAMPLE 1

General process for synthesis of the compounds:
X—(L)—NH—CH($CH_2$—$R_4$)—CO—(S)—Cyt—E The general synthesis process comprises a first step in which the intermediate compound (L)—NH—CH($CH_2$—$R_4$)—CO—(S)—Cyt—E is obtained. The residue X is subsequently added to this using three different synthesis methods.

I. Synthesis of the Intermediate Compound: (L)—NH—CH($CH_2$—$R_4$)—CO—(S)—CytOMe (S)—CytOMe.HCl (1.0 eq) and Boc—NH—CH($CH_2$—$R_4$)—CO—OH (1.1 eq) are solubilized in $CH_3CN$ and cooled in an ice bath. They are then stirred for a few minutes, HBTU (1.2 eq) and TEA (2.2 eq) are added, and the mixture is kept under stirring until it reaches room temperature.

After this, the reaction is concentrated on a rotavapor to which is added $CH_2Cl_2$. Washing is carried out using normal acid-basic treatments. The organic extracts are placed on anhydrous sodium sulphate and then cooled. They are dried, and the product obtained is placed under vacuum on KOH for one night.

Boc—(L)—NH—CH($CH_2$—$R_4$)—CO—(S)—CytOMe (1.0 eq) is taken up with anhydrous dioxane, and the solution, under stirring, is then cooled to 0° C. and brought into an argon atmosphere. Once the temperature has stabilized, 4N HCl (4 eq) in anhydrous dioxane is added dropwise, allowing the temperature of the system to come up to room temperature, maintaining the mixture under stirring and in an argon atmosphere.

The product is concentrated on a rotavapor with anhydrous ethyl ether without peroxides. The residue is taken up with methanol and then precipitated with anhydrous ethyl ether without peroxides. It is then left at room temperature under stirring and then in a cool room.

The precipitate is filtered on G4 and placed under vacuum on $P_2O_5$. (L)—NH—CH($CH_2$—$R_4$)—CO—(S)—CytOMe is obtained.

II. Method (A) for Synthesis of the Compound: X—(L)—(CH$_2$—$R_4$)—CO—(S)—Cyt—OH —NH—CH($CH_2$—$R_4$)—CO—(S)—Cyt—OMe.HCl (1.0 eq) is added to the solution of X—OH acid (1.2 eq) in anhydrous $CH_3CN$. HBTU (1.2 eq) and TES (2.2 eq) are then added.

The reaction is made to proceed until completed. The reaction mixture is concentrated, $CH_2Cl_2$ is added, and it is then treated using normal acid-basic washing. The organic extracts are placed on anhydrous sodium sulphate and then cooled.

The product X—NH—CH($CH_2$—$R_4$)—CO—(S)—Cyt—OMe (1.0 eq) is taken up in $CH_3CN$ and $H_2O$. The solution is cooled in an ice bath under stirring, and 2.0 eq of 0.1N NaOH is added. The solution is made to react for several hours, allowing the temperature to rise to room temperature.

The reaction product is purified on SPE C18. X—(L)—NH—CH($CH_2$—$R_4$)—CO—(S)—Cyt—OH is obtained.

III. Method (B) for Synthesis of the Compound: X—(L)—NH—CH($CH_2$—$R_4$)—CO—(S)—Cyt—OH Pyridine (1.17 eq) and $SOCl_2$ (1.165 eq) are added under an argon flow and under stirring to the solution of X—OH acid DCHA salt (1.0 eq) in anhydrous $CH_2Cl_2$. One minute after addition of the thionyl chloride, (L)—NH—CH($CH_2$—

R$_4$)—CO—(S)—CytOMe.HCl (0.604 eq) and DMAP (1.202 eq) in anhydrous CH$_2$Cl$_2$ are added. On completion of the reaction AcOEt is added, and the organic phase is washed with a saturated solution of NaCl, and subsequently with 10% citric acid and then with 5% bicarbonate. Finally, the organic extracts are washed with a saturated aqueous solution of NaCl until reaching a neutral pH and then placed on anhydrous sodium sulphate and cooled.

The organic solution, containing X—(L)—NH—CH(CH$_2$—R$_4$)—CO—(S)—Cyt—OMe, is dried and then hydrolyzed.

The ester X—NH—CH(CH$_2$—R$_4$)—CO—(S)—Cyt—OMe (1.0 eq) is taken up in CH$_3$CN and H$_2$O. The solution is cooled in an ice bath under stirring, and 0.1N NaOH (2.0 eq) is added. The solution is made to react for several hours, allowing the temperature to rise to room temperature.

The reaction product is purified on SPE C18. X—(L)—NH—CH(CH$_2$—R$_4$)—CO—(S)—Cyt—OH is obtained.

IV. Method (C) for Preparation of the Compound: X—(L)—NH—CH(CH$_2$—R$_4$)—CO—(S)—Cyt—OH —NH—CH(CH$_2$—R$_4$)—CO—(S)—CytOMe.HCl (1.0 eq) and X—OH (1.1 eq) are solubilized in CH$_3$CN and cooled in an ice bath. After stirring for a few minutes, HBTU (1.2 eq) and TEA (2.2 eq) are added, and the mixture is left under stirring, allowing the temperature to rise to room temperature.

On completion of the reaction AcOEt is added, and the organic phase is washed with a saturated aqueous solution of NaCl, and subsequently with 10% citric acid and then with 5% bicarbonate. The organic extracts are finally washed with a saturated aqueous solution of NaCl until reaching neutral pH and then placed on anhydrous sodium sulphate and cooled.

The organic solution, containing X—(L)—NH—CH(CH$_2$—R$_4$)—CO—(S)—Cyt—OMe, is dried out and then hydrolyzed.

The ester X—NH—CH(CH$_2$—R$_4$)—CO—(S)—Cyt—OMe (1.0 eq) is taken up in CH$_3$CN and H$_2$O. The solution is cooled in an ice bath under stirring, and 0.1N NaOH (2.0 eq) is added. The solution is reacted for several hours, allowing the temperature to rise to room temperature.

The reaction product is purified on SPE C18. X—(L)—NH—CH(CH$_2$—R$_4$)—CO—(S)—Cyt—OH is obtained.

V. Particular Syntheses

PIC—(L)—Leu—(L)—Cyt—NHOH

To the solution of 43 mg of PIC—Leu—Cyt—OH (1.0 eq) in 4 ml of anhydrous methylene chloride, 19 mg of HOBT (1.25 eq) and 20.5 mg of DCC (1.0 eq) are added, under stirring and at room temperature.

After 60 minutes the solution is filtered and to the filtrate is added a mixture in methylene chloride (3 ml) of 8.5 mg of hydroxylamine chlorohydrate (1.02 eq) and 17 mcl of triethylamine (1.02 eq). This is stirred for eighteen hours at room temperature and then concentrated on a rotavapor. 20 ml of water are then added, and the mixture is acidified with 2N HCl until reaching pH 2. 10 ml of a saturated solution of sodium chloride are added, and the mixture is extracted twice with 20 ml of ethyl acetate. The combined organic extracts are washed with a saturated solution of sodium chloride until neutral.

The organic phase is then placed on anhydrous sodium sulphate and cooled.

The organic extracts, after drying, are taken up with 5 ml of methanol. The solution obtained in this manner is acidified with 2N HCl to precipitate the excess of starting compound. The solution is filtered and dried, then lyophilized.

The following is obtained: Picolinyl—(L)—Leu—(S)—Cyt—NHOH (abbreviated to PIC—(L)—Leu—(S)—Cyt—NHOH) (yield 50%). (Compound with molecular weight 449.49; empirical formula C$_{24}$H$_{27}$N$_5$O$_4$; Melting point 130° C.; Elementary composition: C=64.23 (theor.64.13), H=6.11 (theor. 6.05), N=15.47 (theor. 15.58).

PIC—(L)—Leu—(S)—Cyt—N—(CH$_3$)—OH

By the same procedure used for synthesis of PIC—(L)—NH—CH(CH$_2$—R$_4$)—CO—(S)—Cyt—NHOH, in which NH—CH(CH$_2$—R$_4$)—CO is equivalent to (L)—Leu and PIC is equivalent to Picolinyl, the product PIC—(L)—Leu—(S)—Cyt—N—(CH$_3$)—OH was prepared. (Compound with molecular weight 463.51, empirical formula C$_{25}$H$_{29}$N$_5$O$_4$; Melting point 145° C.; Elementary composition: C=64.81 (theor. 64.78), H=6.35 (theor. 6.31), N=15.08 (theor. 15.11).

EXAMPLE 2

Synthesis of the Compound 5—MIC—(L)—Cha—(S)—Cyt—OH

I. Synthesis of the Intermediate Compound: Methyl-(S)-1,2,3,4-tetrahydro-9H-pyrrido [3,4-b] indole-3-carboxylate 10 g (1.0 eq) of (L)—Trp—OH and 6.1 ml of 40% formic aldehyde (1.8 eq) were added to 120 ml of a mixture of water and 0.1N sulfuric acid (v/v 2:1), and the mixture was left under stirring for 16 hours at room temperature. At the end of this period the precipitate obtained was filtered on G4, washed using cold water and dried under vacuum on P$_2$O$_5$ for one night. The product (S)-1,2,3,4 tetrahydro-9H-pyrrido [3,4-b]indole-3-carboxylate, abbreviated to (S)—CytOH.H2SO4 (yield 80%), obtained in this way was used for the following step.

(S)—CytOH.H$_2$SO$_4$ equivalent to 8 grams (1.0 eq) and 18.6 ml of chlorotrimethylxylane (abbreviated to TMSCl, 4.0 eq) were added to 90 ml of absolute methanol. The reaction was carried out under argon at room temperature for 30 minutes from addition of the TMSCl and then the temperature was brought to 55° C. and allowed to fall for one night, again under argon.

The reaction was concentrated under vacuum three times with ether, which was anhydrous and free from peroxides. The residue was taken up with 5 ml of methanol and precipitated with anhydrous ether.

The compound was cooled and filtered on G4. The product was dried on P$_2$O$_5$, for one night. (S)—Cyt—OMe—HCl was obtained (yield 87%).

II. Synthesis of the Intermediate Product: (L)—Cha—(S)—CytOMe (S)—Cyt—OMe—HCl equivalent to 128 mg (1.0 eq) and N-(tert-Butoxycarbonyl)—L—(-cyclohexyl—Ala—OH (abbreviated to Boc—Cha) 108 mg (1.1 eq) were added to 10 ml of acetonitrile (CH$_3$CN) cooled in an ice bath, the mixture was stirred for a few minutes and 181 ml of O-Benzotriazol-1-yl-N,N,N',N'-tetramethyluronium hexafluorophosphate (abbreviated to HBTU) (1.2 eq) and 122 mcl of Triethylamine (d=0.726, 2.2 eq) were added, and the whole was left under stirring for 4 hours, allowing the temperature to come up to room temperature. At the end of this time, the reaction was concentrated on a rotavapor until reaching a volume of 8 ml and 90 ml of dichloromethane (CH$_2$Cl$_2$) were added.

The product was washed in 80 ml of brine, and then washed twice in 80 ml of 4% acid potassium sulphate. The product was then washed three times with 80 ml brine until neutral and washed twice with 90 ml of 5% bicarbonate. The product was washed until reaching neutral pH using a salt-saturated solution. The organic extracts were placed on anhydrous sodium sulphate and then cooled.

The resulting compound was dried and the foam obtained was placed under vacuum on KOH for one night. The residue Boc—Cha—(S)—CytOMe was taken up with 8 ml of anhydrous dioxane and the solution, under stirring, was then cooled to 0° C. and brought into an argon atmosphere. Once the temperature had stabilized, 3.1 ml of 4N HCl in anhydrous dioxane were added dropwise, allowing the temperature of the system to reach room temperature, maintaining stirring and argon atmosphere for 4 hours.

The product was concentrated on a rotavapor three times with anhydrous ether without peroxides. The residue was taken up with 3 ml of methanol and then precipitated with 500 ml of anhydrous ether without peroxides. It was then left for one hour at room temperature under stirring, and then for three hours in a cool room.

The precipitate was filtered on G4 and placed under vacuum on $P_2O_5$. Using the same procedure used for synthesis of (L)—NH—CH(CH$_2$—R$_4$)—CO—(S)—Cyt—OMe, in which NH—CH(CH$_2$—R$_4$)—CO is equal to (L)—Cha, the following products were prepared:

HCl.(L)—Trp—(S)—Cyt—OMe
HCl.(L)—Phe—(S)—Cyt—OMe
HCl.(L)—Leu—(S)—Cyt—OMe
HCl.(L)—Asn—(S)—Cyt—OMe
HCl.(L)—Lys(Fmoc)—(S)—Cyt—OMe III. Synthesis of the Compound 5—MIC—Cha—(S)—Cyt—OH According to Method (A)

To the solution of mg 100 5—Methoxy—2—indolecarboxylic acid (Aldrich) (1.1 eq, abbreviated to 5—MIC) in 15 ml of anhydrous acetonitrile (CH$_3$CN), cooled in an ice bath and under stirring, were added 200 mg of Cha—(S)—Cyt—OMe.Cl (1.2 eq). 217 mg of HBTU (Aldrich) (1.2 eq) and 150 mcl of triethylamine (d=0.726, 2.2 eq) were then added.

The reaction was continued for three hours. At the end of this time the mixture was concentrated and 90 ml of methylene chloride were added, after which it was treated using normal acid-basic washing processes.

The organic extracts were placed on anhydrous sodium sulphate and then cooled.

250 mg of product 5—MIC—Cha—Cyt—OMe (1.0 eq) were taken up in 10 ml of acetonitrile and 0.7 ml of water. The solution was cooled in an ice bath under stirring, and then 9.3 ml of 0.1N NaOH (2.0 eq) were added. The solution was stirred for 12 hours, allowing it to rise to room temperature. The reaction was treated in the following manner:

1) Purification from the non-hydrolyzed ester

The reaction solution was loaded onto a 1 g C18 SPE column (Backer), previously buffered with reaction solvent. The eluate containing only the product 5—MIC—Cha—(S)—CytOH was acidified by the addition of 1N HCl, and water was added until the solution became turbid.

2) Purification of the acid

The solution containing the product was subsequently loaded onto 2 SPE columns (Backer) conditioned with the sample acid eluant. The eluate was eliminated and the SPE columns were eluted with methanol.

The combined organic phases were concentrated until reaching a volume of 3 ml and precipitated with 500 ml of 0.1N HCl.

After cooling in a cool chamber, the precipitate was filtered on G4 and under vacuum on $P_2O_5$ (yield 60%). The compound 5—MIC—Cha—(S)—Cyt—OH (Compound 1) was obtained.

EXAMPLE 3

Using the same procedure used for synthesis of 5—MIC—(L)—NH—CH (CH$_2$—R$_4$)—CO—(S)—Cyt—OH, where NH—CH(CH$_2$—R$_4$)—CO is equal to (L)—Cha and 5—MIC is equal to (5-Methoxy-indol-2-yl)carbonyl, the following products were prepared:

TABLE 1

| | |
|---|---|
| 2-PMTA—(L)—Leu—(S)—Cyt—OH | Compound 2 |
| 4-PTA—(L)—Leu—(S)—Cyt—OH | Compound 3 |
| 3-APZC—(L)—Leu—(S)—Cyt—OH | Compound 4 |
| 7-MBF—(L)—Leu—(S)—Cyt—OH | Compound 5 |
| 4-MQC—(L)—Leu—(S)—Cyt—OH | Compound 6 |
| 5-HIC—(L)—Leu—(S)—Cyt—OH | Compound 7 |
| 5-MIC—(L)—Phe—(S)—Cyt—OH | Compound 8 |
| PIC—(L)—Leu—(S)—Cyt—OH | Compound 9 |
| 2-FUR—(L)—Cha—(S)—Cyt—OH | Compound 10 |
| 2-FUR—(L)—Phe—(S)—Cyt—OH | Compound 11 |
| (L)—HomoSer—(L)—Leu—(S)—Cyt—OH | Compound 12 |

Chemical and Physical Characteristics of the Compounds Synthesized Using the Method Described

| No. | Mol. Weight | Formula Unit | Carbon Found | % Theor. | Hydrogen Found | % Theor. | Nitrogen Found | % Theor. | Melting Point °C. |
|---|---|---|---|---|---|---|---|---|---|
| 1 | 542.61 | $C_{31}H_{34}N_4O_5$ | 68.69 | 68.61 | 6.38 | 6.32 | 10.38 | 10.33 | 151 |
| 2 | 481.49 | $C_{24}H_{27}N_5O_4S$ | 60.11 | 59.86 | 5.71 | 5.65 | 14.10 | 14.55 | 90 |
| 3 | 480.50 | $C_{25}H_{28}N_4O_4S$ | 62.52 | 62.49 | 5.91 | 5.87 | 11.61 | 11.66 | 153 |
| 4 | 450.48 | $C_{23}H_{26}N_6O_4$ | 61.41 | 61.32 | 5.88 | 5.82 | 18.61 | 18.66 | 149 |
| 5 | 503.54 | $C_{28}H_{29}N_3O_6$ | 66.84 | 66.78 | 5.87 | 5.80 | 8.29 | 8.35 | 161 |
| 6 | 514.85 | $C_{29}H_{30}N_4O_5$ | 67.76 | 67.69 | 5.92 | 5.88 | 10.76 | 10.89 | 163 |
| 7 | 488.52 | $C_{27}H_{28}N_4O_5$ | 66.42 | 66.38 | 5.82 | 5.78 | 11.38 | 11.47 | 166 |
| 8 | 536.56 | $C_{31}H_{28}N_4O_5$ | 69.45 | 69.39 | 5.32 | 5.26 | 10.36 | 10.44 | 136 |
| 9 | 434.47 | $C_{24}H_{26}N_4O_4$ | 66.44 | 66.34 | 6.09 | 6.03 | 12.73 | 12.90 | 128 |
| 10 | 463.51 | $C_{26}H_{29}N_3O_5$ | 67.43 | 67.37 | 6.39 | 6.31 | 8.98 | 9.07 | 136 |
| 11 | 487.46 | $C_{26}H_{23}N_3O_5$ | 68.34 | 68.26 | 5.16 | 5.07 | 9.01 | 9.19 | 150 |
| 12 | 430.48 | $C_{22}H_{30}N_4O_5$ | 61.42 | 61.38 | 7.04 | 7.02 | 12.98 | 13.01 | 163 |

EXAMPLE 4

Synthesis of the Compound 3-FUR—(L)—Leu—(S)—Cyt—OH According to method (B)

To a solution of 120 mg of 3-Furoic acid DCHA salt (1.0 eq) in 5 ml of anhydrous $CH_2Cl_2$ 39 mcl of pyridine (on potassium carbonate) (1.17 eq) and 35 mcl of $SOCl_2$ (1.165 eq) were added under an argon flow and under stirring. After one minute from addition of the thionyl chloride, 100 mg of (L)—Leu—(S)—CytOMe.$CH_2Cl$ (0.604 eq) and 64 mg of DMAP (1.202 eq) in 3 ml of anhydrous $CH_2Cl_2$ were added.

After one hour, 80 ml of ethyl acetate were added, and the organic phase was washed with a saturated solution of NaCl and subsequently with 10% citric acid (80*2 ml) and then with 5% bicarbonate (80*2 ml). The organic extracts were then washed with a saturated water solution of NaCl (80*3 ml) until reaching a neutral pH and then placed on anhydrous sodium sulphate and cooled.

The organic solution, containing 3-Furoyl—(L)—Leu—(S)—Cyt—OMe, was dried and then hydrolyzed. 118 mg of the product 3-Furoyl—Leu—(S)—Cyt—OMe (1.0 eq) were taken up in 10 ml of $CH_3CN$ and 4.8 ml of $H_2O$. The solution was cooled in an ice bath under stirring, and then 5.2 ml of 0.1N NaOH (2.0 eq) were added. The solution was stirred for 12 hours and then allowed to rise to room temperature.

The reaction was treated as follows:

1) Purification from the non-hydrolyzed ester

The reaction solution was loaded onto a 1 g C18 SPE column (Backer), previously buffered with reaction solvent. The eluate containing only the product 3-Furoyl—(L)—Leu—(S)—Cyt—OH, was acidified by the addition of 1N HCl, and water was added until the solution became turbid.

2) Purification of the acid

The solution containing the product was subsequently loaded onto 2 SPE columns (Backer) conditioned with the sample acid eluant. The eluate was eliminated and the SPE columns were eluted with methanol. The combined organic phases were concentrated until reaching a volume of 3 ml and precipitated with 500 ml of 0.1N HCl.

After cooling in a cool chamber, the precipitate was filtered on G4 and placed under vacuum on $P_2O_5$. The compound 3-Furoyl—(L)—Leu—(S)—Cyt—OH was obtained (abbreviated to 3-FUR —(L)—Leu—(S)—Cyt—OH) (yield 60%) (Compound 13).

EXAMPLE 5

Using the same process used for synthesis of 3-FUR—NH—CH($CH_2$—$R_4$)—CO—(S)—Cyt—OMe, in which NH—CH($CH_2$—$R_4$)—CO is equal to (L)—Leu and 3-FUR is equal to 3-Furoyl, the following products were prepared:

TABLE 2

| | |
|---|---|
| 5-MIC—(L)—Trp—(S)—Cyt—OH | Compound 14 |
| 2-BZF—(L)—Leu—(S)—Cyt—OH | Compound 15 |
| 2-QIC—(L)—Leu—(S)—Cyt—OH | Compound 16 |
| 5-MIC—(L)—Leu—(S)—Cyt—OH | Compound 17 |
| 2-PZC—(L)—Leu—(S)—Cyt—OH | Compound 18 |
| 2-MPA—(L)—Leu—(S)—Cyt—OH | Compound 19 |
| 2-EBZ—(L)—Leu—(S)—Cyt—OH | Compound 20 |
| 5-MPZ—(L)—Leu—(S)—Cyt—OH | Compound 21 |
| 6-MNC—(L)—Leu—(S)—Cyt—OH | Compound 22 |
| 5-MIA—(L)—Leu—(S)—Cyt—OH | Compound 23 |

Chemical and Physical Characteristics of the Compounds Synthesized Using the Method Described

| No. | Mol. Weight | Formula Unit | Carbon Found | % Theor. | Hydrogen Found | % Theor. | Nitrogen Found | % Theor. | Melting Point °C. |
|---|---|---|---|---|---|---|---|---|---|
| 13 | 423.45 | $C_{23}H_{25}N_3O_5$ | 65.31 | 65.23 | 6.00 | 5.95 | 9.89 | 9.92 | 130 |
| 14 | 575.59 | $C_{33}H_{29}N_5O_5$ | 68.91 | 68.86 | 5.12 | 5.08 | 12.11 | 12.17 | 174 |
| 15 | 473.50 | $C_{27}H_{27}N_3O_5$ | 68.52 | 68.48 | 5.79 | 5.75 | 8.81 | 8.87 | 155 |
| 16 | 484.53 | $C_{28}H_{28}N_4O_4$ | 69.51 | 69.40 | 5.85 | 5.82 | 11.44 | 11.56 | 161 |
| 17 | 502.54 | $C_{29}H_{30}N_4O_5$ | 67.03 | 66.92 | 6.06 | 6.02 | 11.08 | 11.15 | 158 |
| 18 | 435.46 | $C_{23}H_{25}N_5O_4$ | 63.50 | 63.43 | 5.81 | 5.79 | 16.10 | 16.08 | 132 |
| 19 | 477.54 | $C_{27}H_{31}N_3O_5$ | 67.91 | 67.90 | 6.60 | 6.49 | 8.76 | 8.80 | 133 |
| 20 | 477.54 | $C_{27}H_{31}N_3O_6$ | 67.21 | 67.90 | 6.59 | 6.49 | 8.7S | 8.79 | 128 |
| 21 | 449.49 | $C_{24}H_{27}N_5O_4$ | 64.21 | 64.13 | 6.10 | 6.05 | 15.48 | 15.58 | 151 |
| 22 | 448.50 | $C_{25}H_{28}N_4O_4$ | 67.02 | 66.95 | 6.34 | 6.29 | 12.39 | 12.49 | 159 |
| 23 | 530.57 | $C_{30}H_{32}N_3O_6$ | 67.98 | 67.91 | 6.12 | 6.08 | 7.87 | 7.92 | 147 |

EXAMPLE 6

Synthesis of the Compound 2,4-DMB—(L)—Leu—(S)—Cyt—OH According to Method (C)

63.4 mg of 2,4-dimethoxybenzoic acid chloride (Aldrich) (1.2 eq) were added to 15 ml of dry, oxide-free $CH_2Cl_2$. The mixture was stirred, and 100 mg of Leu—(S)—Cyt—OMe.HCl (1.0 eq) and 81 mcl of TEA (2.2 eq) were added. The solution was then placed in an ice bath under stirring for 2.5 hours, and then 90 ml of $CH_2Cl_2$ were added. The solution was washed with 80 ml of saturated NaCl solution, then with 50 ml of 0.1N HCl and then three times with 80 ml of saturated NaCl solution until reaching a neutral pH. The organic extracts were placed on anhydrous sodium sulphate in a cold room.

The organic solution, containing 2,4-dimethoxybenzoyl—Leu—(S)—Cyt—OMe, was dried (yield 95%) and then hydrolyzed. 133 mg of ester (1.0 eq) were taken up with 19 ml of $CH_3CN$ and 11.5 ml of $H_2O$ and the solution was cooled in an ice bath, and then 5.23 ml of 0.1N NaOH (2.0 eq) was added. The solution was stirred for six hours, allowing the temperature to rise to room temperature.

At the end of this time the reaction was treated as follows:

1) Purification from the non-hydrolyzed ester

The reaction solution was loaded onto a 1 g C18 SPE column (Backer), previously buffered with reaction solvent. The eluate containing only the product 2,4-Dimethoxybenzoyl—Leu—(S)—Cyt—OMe, was acidified by the addition of 1N HCl and water was added until the solution became turbid.

2) Purification of the acid

The solution containing the product was subsequently loaded onto 2 SPE columns (Backer) conditioned with the sample acid eluant. The eluate was eliminated, and the SPE columns were eluted with methanol. The combined organic phases were concentrated until reaching a volume of 3 ml and precipitated with 500 ml of 0.1N HCl.

After cooling in a cool chamber, the precipitate was filtered on G4 and placed under vacuum on $P_2O_5$. The compound 2,4-Dimethoxybenzoyl—(L)—Leu—(S)—Cyt—OH was obtained (abbreviated to 2,4-DMB—(L)—Leu—(S)—Cyt—OH) (yield 74%) (Compound 24).

EXAMPLE 7

Using the same process used for synthesis of 3-FUR—(L)—NH—CH(CH$_2$—R$_4$)—CO—(S)—Cyt—OMe, in which NH—CH(CH$_2$—R$_4$)—CO is equal to (L)—Leu, and 3-FUR is equal to 3-Furoyl, the following products were prepared:

idae and the Viperidae (for example, hemorrhagins from *Crotalus Atrox, Botropasin*, hemorrhagin from *Agkistrodon Bilineatus*, various hemorrhagins from *Echis Carinatus*). The following is a description of the purification of the hemorrhagin from *Crotalus Adamanteus*, used for preference in the screening tests because of its manageability.

One gram of lyophilized venom (obtained from the American company Sigma Chemical) was dissolved in Tris-HCl buffer solution at pH 8.0 and loaded on a chromatographic column containing DEAE Sephadex A-50 resin. Using as an eluant a gradient of the buffer, containing NaCl in a concentration of 0 to 1M, four main peaks were obtained for the protein fractions present in the venom. These were concentrated and desalinated, and then tested for the presence of metalloproteinases using the method described below.

Fraction I, containing the majority of metalloproteinase activity, was then passed on a chromatographic column containing Sephadex G-150 resin, and eluted with Tris-HCl buffer pH 7.5. Two main peaks were obtained, and the metalloproteinase activity was identified in the first of these. Further purification, to remove extraneous material, was carried out using Sephadex G-75 resin. The enzyme purified in this way was lyophilized and preserved in a freezer unit until use.

The metalloproteinase activity was tested on the fluorimeter (Perkin Elmer LS 50 B), using as a substrate the

TABLE 3

| | |
|---|---|
| 4-MBZ—(L)—Trp—(S)—Cyt—OH | Compound 25 |
| 4-NBZ—(L)—Leu—(S)—Cyt—OH | Compound 26 |
| 4-CBZ—(L)—Leu—(S)—Cyt—OH | Compound 27 |
| 3-NIC—(L)—Leu—(S)—Cyt—OH | Compound 28 |
| 4-NIC—(L)—Leu—(S)—Cyt—OH | Compound 29 |
| 3,4-DMB—(L)—Leu—(S)—Cyt—OH | Compound 30 |
| HDC—(L)—Leu—(S)—Cyt—OH | Compound 31 |
| BZS—(L)—Phe—(S)—Cyt—OH | Compound 32 |
| 4-EBZ—(L)—Leu—(S)—Cyt—OH | Compound 33 |
| 2-FUR—(L)—Trp—(S)—Cyt—OH | Compound 34 |
| 2-FUR—(L)—Asn—(S)—Cyt—OH | Compound 35 |
| 2-FUR—(L)—Lys(Fmoc)—(S)—Cyt—OH | Compound 36 |
| 1-NAF—(L)—Leu—(S)—Cyt—OH | Compound 37 |

Chemical and Physical Characteristics of the Compounds Synthesized Using the Method Described

| No. | Mol. Weight | Formula Unit | Carbon Found | % Theor. | Hydrogen Found | % Theor. | Nitrogen Found | % Theor. | Melting Point °C. |
|---|---|---|---|---|---|---|---|---|---|
| 24 | 493.54 | $C_{27}H_{31}N_3O_6$ | 65.81 | 65.70 | 6.36 | 6.33 | 8.48 | 8.51 | 103 |
| 25 | 463.51 | $C_{26}H_{29}N_3O_5$ | 67.41 | 67.37 | 6.32 | 6.31 | 9.01 | 9.07 | 110 |
| 26 | 478.48 | $C_{25}H_{26}N_4O_6$ | 62.81 | 62.75 | 5.51 | 5.48 | 11.66 | 11.71 | 167 |
| 27 | 467.93 | $C_{25}H_{26}N_3O_4Cl$ | 64.22 | 64.17 | 5.69 | 5.60 | 8.89 | 8.98 | 175 |
| 28 | 434.47 | $C_{24}H_{26}N_4O_4$ | 66.54 | 66.34 | 6.12 | 6.03 | 12.55 | 12.90 | 187 |
| 29 | 434.47 | $C_{24}H_{26}N_4O_4$ | 66.57 | 66.34 | 6.13 | 6.03 | 12.65 | 12.90 | 170 |
| 30 | 493.54 | $C_{27}H_{31}N_3O_6$ | 65.83 | 65.70 | 6.38 | 6.33 | 8.47 | 8.51 | 154 |
| 31 | 461.54 | $C_{27}H_{31}N_3O_4$ | 70.35 | 70.26 | 6.81 | 6.77 | 9.00 | 9.10 | 103 |
| 32 | 459.53 | $C_{24}H_{27}N_3O_5S$ | 61.52 | 61.39 | 5.84 | 5.80 | 8.91 | 8.95 | 142 |
| 33 | 477.54 | $C_{27}H_{31}N_3O_5$ | 68.01 | 67.90 | 6.59 | 6.54 | 8.72 | 8.80 | 148 |
| 34 | 496.50 | $C_{28}H_{24}N_4O_5$ | 67.83 | 67.73 | 4.91 | 4.87 | 11.22 | 11.28 | 152 |
| 35 | 424.39 | $C_{21}H_{20}N_4O_4$ | 59.48 | 59.43 | 4.82 | 4.75 | 13.10 | 13.20 | 188 |
| 36 | 660.69 | $C_{38}H_{36}N_4O_7$ | 69.14 | 69.08 | 5.54 | 5.49 | 8.38 | 8.48 | 177 |
| 37 | 483.54 | $C_{29}H_{29}N_3O_4$ | 71.67 | 72.03 | 6.15 | 6.04 | 8.65 | 8.69 | 151 |

EXAMPLE 8

Inhibition of Compounds on Metalloproteinases Produced from Snake Venom

The compounds according to the present invention were tested on a number of zinc-dependent metalloproteinases extracted from snake venom, belonging both to the Crotalfluorogenous peptide, indicated as SEQ ID NO:1 in the annexed sequence listing, produced by the Bachem Company. Different quantities of the compounds synthesized were added to 5 mcg of enzyme, in a system thermostatically set to 30° C., under stirring. Formation of fluorescent compounds was followed for 30 minutes (excitation: 320 nm; emission: 420 nm), and the curve was compared with the base line, obtained without the addition of the compounds.

TABLE 4

Inhibitory Activity of the Compounds According to the Present Invention on the Enzyme Purified from the Venom of *Crotalus Adamanteus*

| No. | $IC_{50}$ |
|---|---|
| 1 | $2.9 \times 10^{-8}$ |
| 2 | $2.3 \times 10^{-7}$ |
| 3 | $3.6 \times 10^{-7}$ |
| 4 | $5.7 \times 10^{-8}$ |
| 5 | $9.4 \times 10^{-8}$ |
| 6 | $5.0 \times 10^{-8}$ |
| 7 | $2.3 \times 10^{-8}$ |
| 8 | $1.0 \times 10^{-7}$ |
| 9 | $2.7 \times 10^{-8}$ |
| 10 | $2.5 \times 10^{-8}$ |
| 11 | $5.3 \times 10^{-8}$ |
| 12 | $5.0 \times 10^{-6}$ |
| 13 | $4.0 \times 10^{-7}$ |
| 14 | $4.7 \times 10^{-8}$ |
| 15 | $4.0 \times 10^{-8}$ |
| 16 | $2.8 \times 10^{-8}$ |
| 17 | $2.3 \times 10^{-8}$ |
| 18 | $2.1 \times 10^{-7}$ |
| 19 | $2.6 \times 10^{-7}$ |
| 20 | $1.3 \times 10^{-7}$ |
| 21 | $4.4 \times 10^{-8}$ |
| 22 | $1.1 \times 10^{-7}$ |
| 23 | $7.5 \times 10^{-8}$ |
| 24 | $9.8 \times 10^{-8}$ |
| 25 | $5.4 \times 10^{-8}$ |
| 26 | $9.5 \times 10^{-8}$ |
| 27 | $1.0 \times 10^{-7}$ |
| 28 | $1.0 \times 10^{-7}$ |
| 29 | $4.0 \times 10^{-7}$ |
| 30 | $3.8 \times 10^{-7}$ |
| 31 | $2.1 \times 10^{-7}$ |
| 32 | $2.0 \times 10^{-6}$ |
| 33 | $7.0 \times 10^{-8}$ |
| 34 | $4.0 \times 10^{-7}$ |
| 35 | $8.0 \times 10^{-6}$ |
| 36 | $1.0 \times 10^{-7}$ |
| 37 | $2.1 \times 10^{-7}$ |

EXAMPLE 9

The same method described above was used to test the chemical compounds of formula (2) described in WO 92/06108, to which reference is made for identification of the compounds indicated in the following Table 5. All the compounds were found to be good inhibitors of the enzyme, with an $IC_{50}$ of between $1 \times 10^{-5}$ and $1 \times 10^{-7}$M.

TABLE 5

Activity of Certain of the Compounds of Formula (2)[1]

| Compound No. | $IC_{50}$ | | | |
|---|---|---|---|---|
| | Crotalus Adamanteus | Echis Carinatus | Bothrops Atrox | Bothrops Jararaca |
| 3 | $3.6 \times 10^{-7}$ | $2.4 \times 10_{-5}$ | $1.2 \times 10_{-5}$ | $6.5 \times 10_{-6}$ |
| 5 | $9.4 \times 10^{-8}$ | $8.9 \times 10_{-6}$ | $4.1 \times 10_{-6}$ | $3.7 \times 10_{-6}$ |
| 9 | $2.7 \times 10^{-8}$ | $3.5 \times 10_{-6}$ | $2.5 \times 10_{-6}$ | $1.3 \times 10_{-6}$ |
| 15 | $4.0 \times 10^{-8}$ | $2.0 \times 10^{-6}$ | $8.2 \times 10^{-6}$ | $1.4 \times 10^{-5}$ |
| 18 | $2.1 \times 10^{-7}$ | $7.0 \times 10^{-6}$ | $5.2 \times 10^{-6}$ | $8.4 \times 10^{-6}$ |
| 22 | $1.1 \times 10^{-7}$ | $1.4 \times 10^{-5}$ | $3.2 \times 10^{-6}$ | $2.1 \times 10^{-5}$ |

TABLE 5-continued

Activity of Certain of the Compounds of Formula (2)[1]

| Compound No. | $IC_{50}$ | | | |
|---|---|---|---|---|
| | Crotalus Adamanteus | Echis Carinatus | Bothrops Atrox | Bothrops Jararaca |
| 31[2] | $2.1 \times 10^{-7}$ | $1.8 \times 10^{-5}$ | $2.6 \times 10^{-7}$ | $4.2 \times 10^{-6}$ |
| 33[3] | $7.0 \times 10^{-8}$ | $9.0 \times 10^{-7}$ | $7.8 \times 10^{-6}$ | $5.0 \times 10^{-6}$ |

[1]Discussed in WO 92/06108, herein incorporated by reference, synthesized on various metalloproteinases purified from snake venom.
[2]Compound 31 is Z—(L)—Pro—(L)—Ala—(S)—CytOH.
[3]Compound 33 is Z—(L)—Pro—(L)—Ala(9)—Me-(5)-CytoMe.

The results expressed in Tables 4 and 5 testify that the compounds described in the present application, and in WO 92/06108, are all extremely active in inhibiting the enzyme purified from the venom of *Crotalus Adamanteus*, and also show a moderate inhibitory activity with respect to other metalloproteinases purified from the venom of other Crotalidae and Viperidae, so that these compounds can be considered inhibitors of the whole class of snake venom metalloproteinases.

EXAMPLE 10

In Vitro Effects on Recombinant Human Gelatinase A.

Assays on human gelatinase A, an enzyme released in high concentration by any kind of tumor cells during the process of metastatization, and recognized also as a product of stimulated cells in many pathological processes, have been performed using the protein obtained by recombinant biotechnology (Strangeways Laboratories, Cambridge, UK). The enzymatic activity has been followed over time, measuring the amount of fluorescent substrate cleaved by the enzyme, in the presence or absence of synthetic compounds (Perkin Elmer L50 B fluorimeter).

TABLE 6

| Compound | Concentration | % Inhibition |
|---|---|---|
| 1 | $7.0 \times 10^{-7}$M | 25 |
| 11 | $8.7 \times 10^{-7}$M | 40 |
| 13 | $9.4 \times 10^{-7}$M | 41 |
| 14 | $6.0 \times 10^{-7}$M | 37 |
| 16 | $8.0 \times 10^{-7}$M | 23 |
| 22 | $8.0 \times 10^{-7}$M | 47 |
| 23 | $8.0 \times 10^{-7}$M | 40 |
| 31 | $8.0 \times 10^{-7}$M | 30 |
| Z—Pro—Leu—Cyt | $1.8 \times 10^{-7}$M | 64 |
| FUR—Leu—Trp | $1.0 \times 10^{-7}$M | 41 |
| Tiof—Leu—Trp | $8.0 \times 10^{-6}$M | 60 |
| Pirr—Leu—Trp | $9.0 \times 10^{-6}$M | 33 |
| MePro—Ala—Cyt | $9.0 \times 10^{-6}$M | 39 |
| Z—Pip—Leu—Trp | $9.0 \times 10^{-6}$M | 63 |

The obtained results indicate that compounds of the present invention, as well as those described in the PCT patent WO 92/6108, are powerful inhibitors both of snake venom hemorrhagic factors and of human gelatinase A, an enzyme heavily involved in pathological disturbances.

EXAMPLE 11

In Vitro Effects on Recombinant Human Gelatinase B

Assays on human gelatinase B, another enzyme released by tumor cells, were performed using also, in this case, the protein obtained by recombinant biotechnology Stangeways Laboratories, Cambridge, UK). As usual, the enzymatic activity was followed over time, measuring the amount of fluorescent substrate cleaved by the enzyme, in the presence or absence of synthetic compounds (Perkin Elmer L50 B fluorimeter).

TABLE 7

| Compound | Concentration | % Inhibition |
|---|---|---|
| 9 | $1.1 \times 10^{-5}$M | 20 |
| 10 | $1.1 \times 10^{-5}$M | 32 |
| 16 | $1.0 \times 10^{-5}$M | 51 |
| 21 | $5.5 \times 10^{-6}$M | 43 |
| 24 | $1.0 \times 10^{-5}$M | 48 |
| 32 | $1.0 \times 10^{-5}$M | 42 |
| Z—Pro—Leu—Cyt | $9.0 \times 10^{-6}$M | 32 |
| 2-FUR—Leu—Trp | $1.0 \times 10^{-5}$M | 22 |
| MePro—Leu—Cyt | $1.1 \times 10^{-5}$M | 37 |

The above results indicate that gelatinase B, another enzyme produced by human cells during pathological reactions, can also be inhibited by compounds of the present invention, as well as compounds disclosed in WO 92/06108.

EXAMPLE 12

In Vitro Assays on Recombinant Human Collagenase

Using the same enzymatic determination already described (fluorimetric detection of cleavage of a substrate peptide containing a fluorescent moiety), some of the compounds were tested on neutrophil collagenase, an enzyme described as participating in any kind of inflammatory reaction in mammalian bodies. In this case, the purified enxzyme was also obtained by recombinant means.

TABLE 8

| Compound | Concentration | % Inhibition |
|---|---|---|
| 10 | $2.1 \times 10^{-5}$M | 51 |
| 11 | $2.2 \times 10^{-5}$M | 27 |
| 24 | $2.0 \times 10^{-5}$M | 19 |
| 25 | $5.2 \times 10^{-5}$M | 23 |
| 27 | $2.1 \times 10^{-5}$M | 28 |
| Z—Pro—Leu—Cyt | $1.8 \times 10^{-5}$M | 23 |
| 2-FUR—Leu—Trp | $2.4 \times 10^{-5}$M | 12 |
| Pirr—Leu—Trp | $1.1 \times 10^{-5}$M | 15 |

The above results show inhibitory activity against one of the most important enzymes produced by human cells during inflammatory reactions.

EXAMPLE 13

In Vitro Activity on Tumor Necrosis Factor (TNF)

It is well known that TNF plays a fundamental role in certain physiological defense responses but, on the other hand, causes severe damage when it is released into circulation in excessive amounts or for prolonged periods. Recently, it was demonstrated that TNF is produced in an active form on the cell surface thanks to a zinc-dependent metalloproteinase. An attempt was, therefore, made to see whether certain compounds selected from among those of the present application and of WO 92/06108 were capable of blocking the release of active TNF in human cell culture medium (Jurkat). The cells were incubated in the presence or in the absence of metalloproteinase inhibitor for 72 hours; the release of TNF was then stimulated using activators (PMA and ionophore calcium), and the Factor was dosed into the culture medium using the ELISA test (Genzyme).

Compounds 9, 10 and 25 of the present invention all showed a dose-dependent inhibitor effect on TNF release by cells, although to a different extent (Compound 9 showed an $IC_{50}$ of around 8 mcg/ml; Compound 10 around 200 mcg/ml; and Compound 25 around 0.7 mcg/ml). Furthermore, the compound Z—Pro—Leu—Cyt (described in Example 1 of WO 92/06108) also showed itself to be active, with an $IC_{50}$ of around 5 mcg/ml. This compound was also made to undergo another test to evaluate TNF release from another strain of human cells in culture (clone T). In this case, inhibitory activity was also seen ($IC_{50}$ lower than 1 mcg/ml).

These results demonstrate that snake venom metalloproteinase inhibitors are capable of blocking TNF release from human cells and are, therefore, potentially useable for treatment in a number of pathological situations, which range from rheumatoid arthritis (and other forms of arthritis) to septic shock, multiple sclerosis, and immunodeficiency caused by viral infections.

EXAMPLE 14

In Vivo Activity on TNF

The same compounds used in the in vitro tests were also made to undergo tests to see whether they were capable of blocking mortality induced in mice of the strain Balb/c by means of lethal doses of LPS (a bacterial agent that stimulates the release of TNF). All the compounds showed themselves to be capable of protecting the mice from death, with an $IC_{50}$ varying from 0.5 to 5 mcg/mouse (i.p. injection).

These results confirm the potential use of the snake venom metalloproteinase inhibitors of the present invention in all pathological situations caused by TNF.

EXAMPLE 15

Activity on Human Collagenase

The compounds of the present invention and those of WO 92/06108 were tested on the enzyme collagenase purified from human neutrophils. Over half of the compounds showed themselves capable of strongly inhibiting the enzyme, which is also known to be directly connected with inflammatory response (rheumatoid arthritis, osteoarthrosis, etc.), tumoral invasion, wound healing, periodontitis, corneal ulcers, etc.

For this reason it can be stated that the inhibition test on snake venom metalloproteinases is highly predictive of an inhibitory activity on the collagenase produced by human cells and makes it possible to predict important therapeutic activity in connection with the inhibition itself.

EXAMPLE 16

Inhibition of Hemorrhages Induced by Snake Venom

The compound 2-FUR—Leu—Trp (described in Example 8 of WO 92/06108), an excellent in vitro inhibitor of the metalloproteinase purified from the venom of *Crotalus Adamanteus*, was made to undergo in vivo testing on mice to test its ability to antagonize the hemorrhages and lethal results induced by snake venom. The results have shown that the compound, incubated with the hemorrhagic factors of various snake venom, is capable of neutralizing the toxic effects thereof. Furthermore, at a dose of 33 mcg/mouse the compound is capable of protecting the mice from death by injection of the venom, even when administered after the venom itself (up to 30 minutes).

Other compounds from the above-mentioned PCT publication WO 92/06108 and from the present application are capable of antagonizing the toxic and lethal effects of snake venom (Crotalidae and Viperidae), although not as strongly.

It can, therefore, be stated that the snake venom metalloproteinase inhibitors form a new class of synthetic antivenom drugs for use in case of poisoning by snakes of the families Crotalidae and Viperidae.

EXAMPLE 17

Effects on Histamine-Induced Microhemorrhages

The compound Z—Pro—Leu—Cyt, described as Example 1 of WO 92/06018, was investigated using the model of capillary permeability variation induced in hamsters following administration of histamine.

This model is generally useful in observing compounds with potential activity on the microcirculation and on arteriosclerosis phenomena. Furthermore, in the administration of histamine induced microhemorrhages at the arteriole level, in a manner similar to that seen in the case of administration of snake venom hemorrhagic factors, using this model it is possible to evaluate whether or not the compounds being studied are capable of interacting with endogenous metalloproteinases in mammals, which are responsible for the effects of histamine.

The results underlined the fact that the compound is extremely powerful in blocking microhemorrhages induced by histamine, both when injected intravenously and when administered orally. In both cases, the dose capable of blocking 50% of effects was around 50 mcg/Kg.

Other compounds of the present invention and of WO 92/06108 also showed themselves capable of inhibiting microhemorrhages induced by histamine in hamsters, although at slightly higher concentrations.

Inhibitors of snake venom metalloproteinases thus have been shown to be capable of antagonizing the pathological processes that lead to internal microhemorrhages, and are, therefore, of use in arteriosclerosis and in a number of other pathological conditions deriving from lesions of the vascular tissue.

EXAMPLE 18

Effects on Infiltrations in the Bronco-Pulmonary Tissue

As the metalloproteinases produced by the cells of mammals are of fundamental importance to allow the cells to migrate from one tissue to another within the organism, Compounds 9, 18, 25 and 31 of the present invention, together with the compounds Z—Pro—Leu—Cyt and FUR—Leu—Cyt (Examples 1 and 8, respectively, of WO 92/06018) were tested on hypereosinophilia induced in rats by Sephadex G-200 resin. The results obtained demonstrate that all the compounds, although to varying degrees, interfered with the number of blood cells that migrate to the inflamed site, inhibiting the motility of one or more of the classes of cell analyzed (lymphocytes, neutrophils, eosinophils, macrophages).

It can, therefore, be concluded that the snake venom metalloproteinase inhibitors are capable of acting on the motility of the cells involved in the inflammatory response at a bronco-pulmonary level, and may be of therapeutic use in the numerous bronco-pulmonary conditions caused by metalloproteinases, including pulmonary emphysema, adult respiratory deficiency syndrome (ARDS), interstitial fibrosis, granulomatose sickness, tumor of the lung and pleurisy.

EXAMPLE 19

Immunologic Effects

Many of the compounds described in the present application were tested in immune response tests to check whether they were capable of influencing progress of the response. The results obtained demonstrate that all the compounds are capable of stimulating the immune response, in a more or less marked manner, expressed as the proliferation of T lymphocytes. Furthermore, many of the compounds showed themselves capable of increasing the response to the influenza virus, determined by the presence of antibodies specific to that virus. Finally, in the contact sensitivity test (related to allergic response) it was found that many of the compounds were powerful inhibitors of the response.

It can, therefore, be concluded that snake venom metalloproteinase inhibitors are capable of significantly influencing the immune responses of mammals, both increasing the proliferation of T lymphocytes and increasing the production of antibodies. Furthermore, they are capable of blocking allergic type responses.

EXAMPLE 20

Inhibition of Human Melanoma Cell Invasion through Matrigel

In order to obtain information about the possible interference of the synthesized compounds on the ability of tumor cells to migrate through the body (metastatization), the human melanoma cell line VMM-5 was used in the matrigel-based invasion assay, in which basal membrane matrigel (Becton Dickinson) and tissue culture inserts with 8 microns pore size in 24 well tissue culture plates were used as Boyden chambers. The chambers were coated with diluted matrigel and allowed to dry overnight; they were then reconstituted with serum free medium, and melanoma cells (4,000,000/ml) were dispensed in each insert. In the lower chambers, a chemoattractant was included. The chambers were finally placed in a humidified $CO_2$ incubator at 37° C., and incubated for 20 hours. The inserts were dried and the cells on the upper surface removed. The polycarbonate filters were fixed with methanol, stained with hematoxylin and eosin, and counted with a microscope. Inhibition of migration due to compounds has been expressed as a percentage of the total number of migrated cells in the control chambers containing only the buffer in which the compounds were dissolved.

TABLE 9

| Compound | Concentration (micro M) | % Inhibition of Invasion |
| --- | --- | --- |
| 3 | 500 | 69 |
| 9 | 500 | 94 |
| 10 | 500 | 99 |
| 24 | 500 | 100 |
| Z—Pro—Leu—Cyt | 500 | 70 |
| FUR—Leu—Cyt | 500 | 69 |
| MePro—Leu—Cyt | 500 | 40 |

The above results show that compounds of the present invention as well as those reported in the PCT publication WO 92/06108, are strong inhibitors of cancer cell motility and, therefore, can be utilized as inhibitors of metastatization processes in patients affected by tumors.

EXAMPLE 21

Resistance to Proteolytic Activity in Stomach Juices

To check if the compounds of the present invention are resistant to proteolytic activity in stomach juices and, therefore, could be administered orally, the stomachs of fasting rats were homogenized in physiological solutions (1:1). 300 microliters of solutions of the compounds (1 mg/ml of saline) were incubated with 0.5 ml of stomach homogenates (37° C.). The reaction was blocked through addition of 1.5 ml methanol and, after centrifugation, 10 microliters were injected in an HPLC apparatus against the standard solutions of compounds, in order to measure the amount of remaining

TABLE 10

| Compound | Residue after 60 Minutes | Residue after 120 Minutes |
|---|---|---|
| 3 | 100% | >95% |
| 10 | 100% | >95% |
| 11 | 100% | >95% |
| 26 | 100% | >95% |
| 30 | 100% | >95% |
| 33 | 100% | >95% |

These results show that the compounds of the present invention according to formula (1) can be administered orally and are capable of resisting the effects of hydrochloric acid and proteolytic enzymes present in the stomach, in contrast to natural peptides. In these peptidomimetic compounds of the present invention, the peptide bond is protected or replaced with a non-peptide bond.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for determining the therapeutic potential of a peptidomimetic compound as an inhibitor of zinc-dependent metalloproteinase activity associated with pathological conditions of humans and animals, comprising the steps of:

(a) conducting a first enzyme inhibition test and determining a first level of inhibitory activity of peptidomimetic compounds as inhibitors of a zinc-dependent metalloproteinase extracted from the venom of snakes belonging to the families Crotalidae and Viperidae;

(b) screening said compounds on the basis of said first level of inhibitory activity by assessing whether each of said compounds has an inhibitory activity on said zinc-dependent metalloproteinase from snake venom expressed in terms of an $IC_{50}$ not greater than $10^{-5}M$;

(c) conducting a second enzyme inhibition test and determining a second level of inhibitory activity of said compounds as inhibitors of zinc-dependent metalloproteinase endogenous in a mammal, the activity of said zinc-dependent metalloproteinase being associated with at least one pathological condition in said mammal;

(d) screening said compounds on the basis of said second level of inhibitory activity by assessing whether each of said compounds has an inhibitory activity on said zinc-dependent metalloproteinase endogenous in mammals expressed in terms of an $IC_{50}$ not greater than $10^{-5}M$;

whereby
step (a) and step (b) make a primary selection of the tested compounds as inhibitors of zinc-dependent metalloproteinases form snake venom and therefore as potential inhibitors of zinc-dependent metalloproteinases in mammals;
step (c) and step d) test the capability of said selected compounds for inhibiting the zinc-dependent metalloproteinases associated with at least one pathological condition in mammals, and
the pharmacological activity against said at least one pathological condition of the compounds screened thereby is verified by pharmacological tests.

2. The method according to claim 1, wherein said zinc-dependent metalloproteinase extracted from the venom of snakes is selected from hemorrhagines of *Crotalus Atrox*, botropasine and hemorrhagines from *Agkistrodon Bilneatus*, and hemorrhagines from *Echis Carinatus*.

3. The method according to claim 1, wherein said zinc-dependent metalloproteinase endogenous in a mammal is selected from matrixins, collagenases, gelatinases, and a metalloproteinase processing TNF-alpha.

4. The method according to claim 1 in which said peptidomimetic compound is selected from the group of peptidomimetic compounds

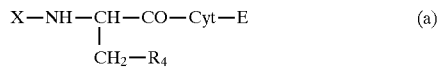

where:

E indicates OH, $NH_2$, NHOH, $N(CH_3)OH$, or esters;

$R_4$ may be $CH-(CH_3)_2$, indol-2-yl, phenyl, cyclohexyl, $CO-NH_2$ or $(CH_2)_3-NH-Fmoc$;

X may be Xa, Xb, Xc, 5-methoxy-1-indanone-3acetyl, naphtoyl, or homoseryl, where Xa is

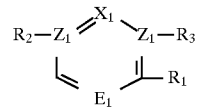

wherein
$X_1$ is CH, N, or C—OMe;
$E_1$ is CH or N;
$Z_1$ is C or N;
$R_1$ is CO, $(CH_2)_2$—CO, $SO_2$, $CH_2$—CO, or $SOCH_2$—CO;
$R_2$ is OMe, H, $NO_2$, Cl, OEt, or $CH_3$;
$R_3$ is OEt, H or OMe, with the proviso that where $Z_1$, is N, $R_2$ and $R_3$ are not present; Xb is

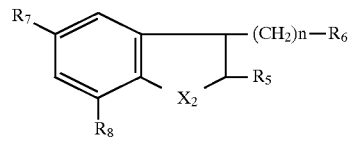

wherein
$X_2$ is O,N, or NH;
n is 1 or 2;
$R_6$ is H;
$R_7$ is H, OH, OMe, or Cl;
$R_8$ is H or OMe;
$R_9$ is CO;
Xc is

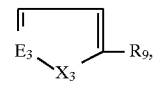

wherein
$X_3$ is O or $CH_2$;
$E_3$ is O or CH;
$R_9$ is CO;
and (b) Q—B—T wherein Q is a monovalent radical of a ring molecule selected from the group consisting of

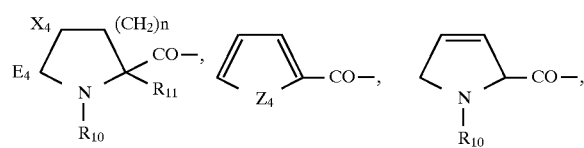

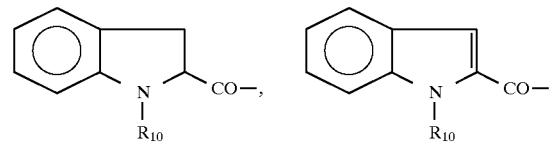

and

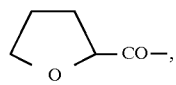

wherein

X$_4$ is CH$_2$, S, or CHOH;

n is 0, 1 or 2;

R$_{11}$ is H or CH$_3$;

R$_{10}$ is H, CH$_3$ or a group used in peptide synthesis that blocks 1' nitrogen atom;

E$_4$ is CH$_2$ or CO; and;

Z$_4$ is NH, NCH$_3$, O, or S;

B is a bivalent radical of an (L)-alpha-amino acid selected from glycine, leucine, alanine or valine; and T is a monovalent radical of an aromatic (L)-amino acid selected from tryptophan, phenylalanine, or phenylglycine;

or T is a monovalent radical selected from the group consisting of

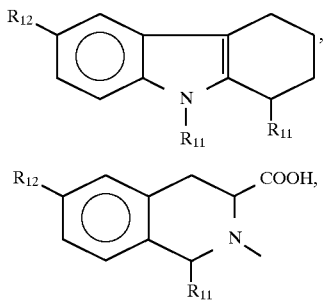

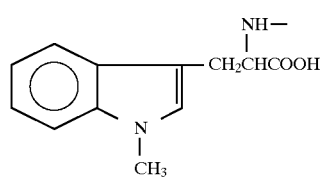

and

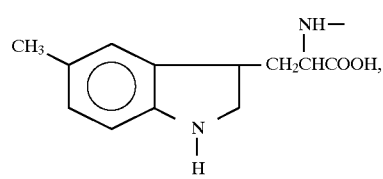

wherein

R$_{11}$ is H or CH$_3$; and

R$_{12}$ is H, OH, OCH$_3$, or CH$_3$; and pharmaceutically acceptable salts, esters and amides of all of the compounds listed above.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( D ) OTHER INFORMATION:/note= Xaa in position 1 is an alanine
           which links a 2-aminobenzoyl group; Xaa in position 4
           is an alanine which links a nitrobenzylamide ( x i ) SEQUENCE DESCRIPTION: SEQ ID NO: 1:

Xaa   Gly   Leu   Xaa